US007867781B2

(12) United States Patent
Schelp et al.

(10) Patent No.: US 7,867,781 B2
(45) Date of Patent: Jan. 11, 2011

(54) DETECTION METHODS

(75) Inventors: Carsten Schelp, Hockessin, DE (US); Hans-Erwin Pauly, Dautphetal (DE)

(73) Assignee: Siemens Healthcare Diagnostics Products GmbH, Marburg (DE)

(*) Notice: Subject to any disclaimer, the term of this patent is extended or adjusted under 35 U.S.C. 154(b) by 842 days.

(21) Appl. No.: 10/024,258

(22) Filed: Dec. 21, 2001

(65) Prior Publication Data

US 2010/0311185 A1 Dec. 9, 2010

(30) Foreign Application Priority Data

Dec. 22, 2000 (DE) ............................... 100 64 827

(51) Int. Cl.
*G01N 33/543* (2006.01)
(52) U.S. Cl. ...................... 436/518; 435/7.1; 435/7.92; 436/501
(58) Field of Classification Search ................. 436/518, 436/6; 435/7.1, 7.9, 188, 7.92, 7.94, 174, 435/287.9; 506/4, 6, 9
See application file for complete search history.

(56) References Cited

U.S. PATENT DOCUMENTS

| | | | |
|---|---|---|---|
| 3,996,345 A | 12/1976 | Ullman et al. ................. 424/12 |
| 4,166,102 A | 8/1979 | Johnson | |
| 4,228,237 A * | 10/1980 | Hevey et al. ................... 435/5 |
| 4,264,766 A | 4/1981 | Fischer | |
| 4,450,231 A | 5/1984 | Ozkan | |
| 4,452,773 A | 6/1984 | Molday | |
| 4,590,169 A | 5/1986 | Cragle et al. ................. 436/523 |
| 4,595,661 A | 6/1986 | Cragle et al. ................. 436/534 |
| 4,650,751 A | 3/1987 | Siegal et al. | |
| 4,914,040 A | 4/1990 | Lenz et al. | |
| 5,177,059 A | 1/1993 | Handley et al. | |
| 5,340,716 A | 8/1994 | Ullman et al. ................. 435/6 |
| 5,437,983 A * | 8/1995 | Watts et al. ................... 435/7.5 |
| 5,545,834 A | 8/1996 | Singh et al. ................... 544/6 |
| 5,641,629 A * | 6/1997 | Pitner et al. ................... 435/6 |
| 5,728,588 A | 3/1998 | Caldwell et al. | |
| 5,739,042 A * | 4/1998 | Frengen ....................... 436/523 |
| 5,776,706 A | 7/1998 | Siiman et al. | |
| 5,981,180 A * | 11/1999 | Chandler et al. ............... 435/6 |
| 6,011,008 A | 1/2000 | Domb et al. | |
| 6,187,594 B1 | 2/2001 | Kraus et al. ................... 436/69 |
| 6,399,317 B1 | 6/2002 | Weimer | |
| 6,489,309 B1 | 12/2002 | Singh et al. | |
| 6,500,930 B2 | 12/2002 | Adamson | |
| 6,610,494 B2 * | 8/2003 | Marquardt et al. ............ 435/7.1 |
| 6,646,120 B1 | 11/2003 | Chaubet et al. | |
| 2002/0034827 A1 | 3/2002 | Singh et al. | |
| 2003/0190760 A1 | 10/2003 | Watkins et al. | |
| 2004/0043508 A1 | 3/2004 | Frutos et al. | |

FOREIGN PATENT DOCUMENTS

| | | |
|---|---|---|
| CA | 2193344 | 6/1997 |
| EP | 0 080 614 A2 | 6/1983 |
| EP | 0 227 054 B1 | 7/1987 |
| EP | 0 246 446 B1 | 11/1987 |
| EP | 0 263 401 B1 | 4/1988 |
| EP | 0 411 945 A2 | 2/1991 |
| EP | 0 515 194 A2 | 11/1992 |
| EP | 0 603 958 A1 | 6/1994 |
| EP | 0 617 285 A2 | 9/1994 |
| EP | 0 781 998 A2 | 7/1997 |
| EP | 0 787 986 A1 | 8/1997 |
| JP | A-60-501776 | 10/1985 |
| JP | A-63-096557 | 4/1988 |
| WO | WO 95/06877 | 3/1995 |
| WO | WO 95/25172 | 9/1995 |

OTHER PUBLICATIONS

Pekka Palomaki, Simultaneous use of poly- and monoclonal antibodies as enzyme tracers in a one-step enxyme immunoassay for the detection of hepatitis B surface antigen, JOurnal of Immunological Methods, vol. 145 (1991) pp. 55-63.*

Meinecke, R. & Meyer, B. Determination of the binding specificity of an integral membrane protein by saturation transfer difference NMR: RGD peptide ligands binding to integrin $\alpha_{IIb}\beta_3$. J. Med. Chem. 2001;44:3059-3065.*

(Continued)

*Primary Examiner*—Melanie J. Yu
*Assistant Examiner*—Gary W Counts
(74) *Attorney, Agent, or Firm*—Finnegan, Henderson, Farabow, Garrett & Dunner, L.L.P.

(57) ABSTRACT

The invention relates to a method for quantitatively or qualitatively detecting an analyte in a sample, with the sample being incubated, for the purpose of avoiding, diminishing and/or detecting the high-dose hook effect, with an analyte-specific binding partner R1, which is associated with a solid phase, an analyte-specific binding partner R2, which is associated with a label L1, and an analyte-specific binding partner R3, which is associated with a label L2, and the L1-dependent measurement signal being determined either at a different time from the L2-dependent or L1 plus L2-dependent measurement signal or using a different measurement method.

46 Claims, 2 Drawing Sheets

OTHER PUBLICATIONS

Figure 1:
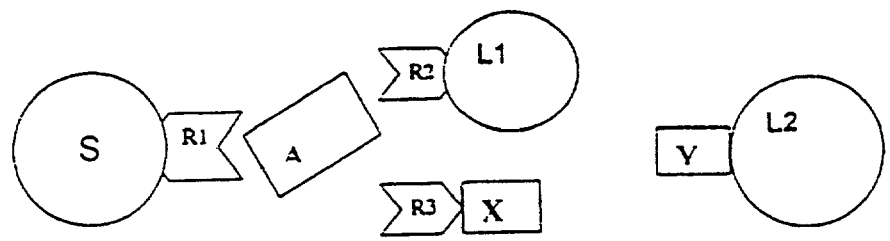

Klein, J. et al. Detecting binding affinity to immobilized receptor proteins in compound libraries by HR-MAS STD NMR. J. Am. Chem. Soc. 1999;121:5336-5337.*

Daniel, C. & Wood, F.S., One Independent Variable, in Fitting Equations to Data, 2nd Ed., Chapter 3, pp. 19-49, John Wiley & Sons, Inc. (1980).*

Buraida et al., Peptides, Antibodies, and FRET on Beads in Flow Cytometry: A Model System Using Fluoresceinated and Biotinylated B-Endorphin, Cytometry, 37:21-31, 1999.*

Ullman et al., Luminescent oxygen channeling immunoassay: Measurment of particle binding kinetcs by chemiluminescence, Proc. Natl. Acad. Sci. USA, vol. 91, pp. 5426-5430 1994.*

Bayer et al., The Avidin-Biotin System Immunoassay, Chapter 11, 1996, pp. 237-267.*

Papik, K., et al; "Automated Prozone Effect Detection in Ferritin Homogeneous Immunoassays Using Neural Network Classifiers;" *Clin Chem Lab Med*, 37(4), pp. 471-476 (1999).

Larrick, J. W., et al.; "Recombinant Antibodies;" Hum. Antibod. Hybridomas, vol. 2, pp. 172-189 (1991).

Messerschmid, S.; "Erzeugung Von Polyklonalen Antikörpern in Nicht-Säugern;" *BIOforum*, pp. 500-502 (1996).

Fischer, R., et al.; "Molecular Farming of Recombinant Antibodies in Plants;" Biol. Chem., vol. 380, pp. 825-839 (1999).

Hiatt, A., et al.; "Assembly of Antibodies and Mutagenized Variants in Transgenic Plants and Plant Cell Cultures;" Genetic Engineering, vol. 14, pp. 49-64 (1992).

Bailey, M. P., et al.; "On the Use of Fluorescent Labels in Immunoassay;" Journal of Pharmaceutical & Biomedical Analysis, vol. 5, No. 7, pp. 649-658 (1987).

Udenfriend, S., et al.; "Scintillation Proximity Radioimmunoassay Utilizing $^{125}$I-labeled Ligands;" *Proc. Natl. Acad. Sci, USA*, vol. 82, pp. 8672-8676 (1985).

Mathis, G.; "Rare Earth Cryptates and Homogeneous Fluoroimmunoassays With Human Sera;" Clin. Chem, vol. 39, No. 9, pp. 1953-1959 (1993).

Boguslaski, R. C., et al.; "Homogeneous Immunoassays;" Applied Biochemistry and Biotechnology, vol. 7, pp. 401-414 (1982).

Ullman, E. F., et al.; "Luminescent Oxygen Channeling Immunoassay: Measurement of Particle Binding Kinetics by Chemiluminescence;" Proc. Natl. Acad. Sci, USA, vol. 91, pp. 5426-5430 (1994).

Ullman, E. F., et al.; "Luminescent Oxygen Channeling Assay (LOCI™): Sensitive, Broadly Applicable Homogeneous Immunoassay Method;" Clinical Chemistry, vol. 42, No. 9, pp. 1518-1526 (1996).

Eriksson, S., et al.; "Dual-Label Time-Resolved Immunofluorometric Assay of Free and Total Prostate-Specific Antigen Based on Recombinant Fab Fragments;" Clinical Chemistry, vol. 46, No. 5, pp. 658-666 (2000).

European Search Report for EP 1 219 964 A1, dated Jan. 30, 2002, Jan. 30, 2002.

Dispatch No. 360369 (Notification of Reasons for Refusal in Application No. 2001-389544), dated Aug. 22, 2006.

English language abstract of EP 0 263 401 (German language counterpart of JP-A-63-096557), published Apr. 13, 1988.

European Search Report for EP 1 219 964 A1, dated Jan. 30, 2002.

Dispatch No. 360369 (Notification of Reasons for Refusal in Application No. 2001-389544), dated Aug. 22, 2006.

English language abstract of EP 0 263 401 (German language counterpart of JP-A-63-096557), published Apr. 13, 1988.

* cited by examiner

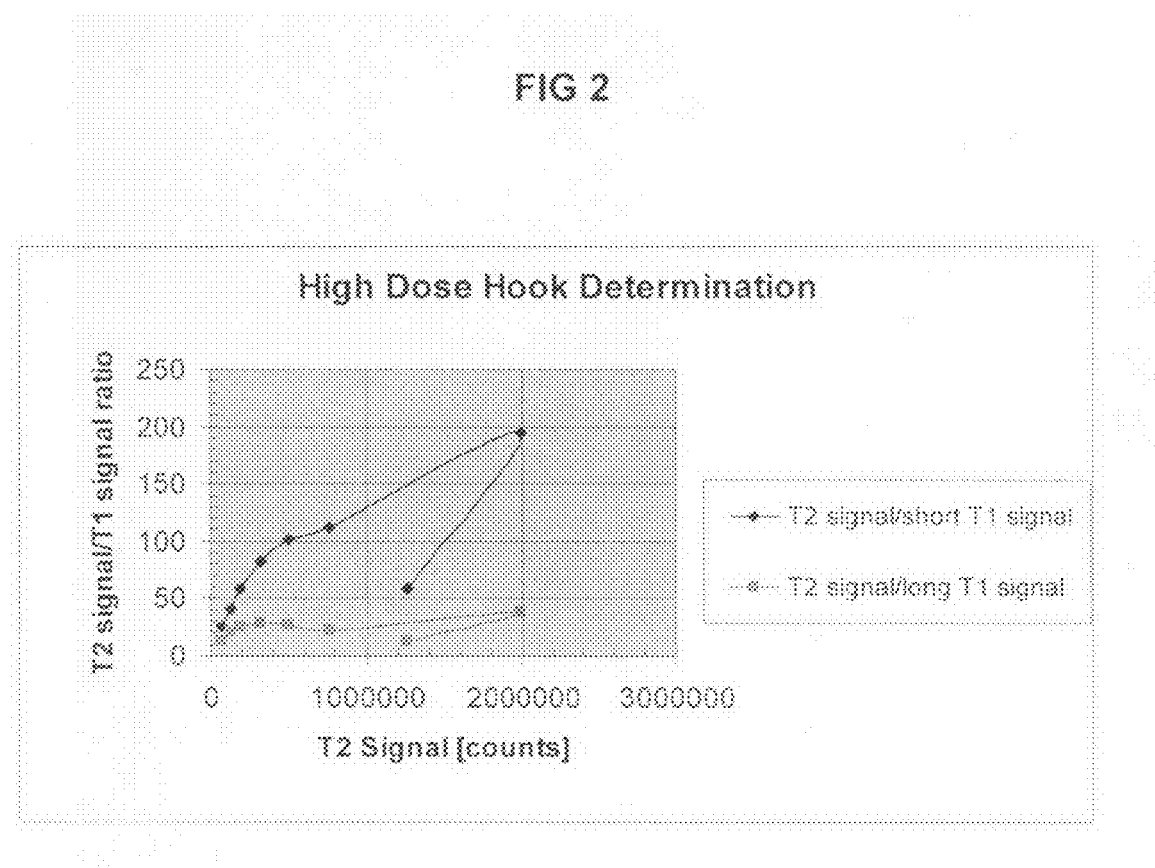

DETECTION METHODS

The invention relates to methods for quantitatively or qualitatively detecting an analyte in a sample.

A variety of test methods, for example what are termed sandwich immunoassays, are employed for detecting analytes. In such an immunoassay, two antibodies bind to two epitopes on the analyte to be detected, such that a "sandwich complex" is formed.

In a heterogeneous sandwich immunoassay, one of the antibodies is bound to a solid phase (e.g. a macrotitration plate, magnetic particles, etc.) and is used for separating off the sandwich complex from the liquid phase, while the other antibody carries a detectable label (e.g. an enzyme, a fluorescent label, a chemiluminescent label, etc.) for the purpose of detecting the immune complex. These test methods are further subdivided into what are termed single-step sandwich immunoassays, in which the two antibody reagents are incubated with the sample simultaneously, and two-step sandwich immunoassays, in which the sample is firstly incubated with the solid phase reagent and, after a separation and washing step, the solid phase-bound antibody-antigen complex is incubated with the detection reagent.

In a homogeneous sandwich immunoassay, such as a nephelometric latex test, the antibody reagents are incubated together with the sample, and measured, without a separation or washing step being carried out at any point in the method. Expressed in other words: no separation of the antibody-bound analyte from the free analyte takes place.

Like the homogeneous sandwich immunoassay, the single-step immunoassay has the advantage that it can be carried out more rapidly and can be automated more readily. However, a fundamental problem arises in the case of these test methods if the concentration of the analyte in the sample is very high. For example, analytes such as albumin, immunoglobulins, $\beta$2-microglobulin, human chorionic gonadotropin (hCG), ferritin and alpha-fetoprotein (AFP) are known to be present at very high concentrations in samples. If unbound analyte is not removed, as it is in the two-step sandwich immunoassay, prior to incubation with the labeled antibody, the binding sites of the antibodies can become saturated without a sandwich complex having been formed. In the case of samples containing increasing concentrations of analyte, this results in the measurement signal initially increasing and then decreasing once again from a particular limit concentration onwards (see, e.g., FIG. 1 in Papik et al. (1999) Clin. Chem. Lab. Med., 37: 471-476). This phenomenon, which is also known as the "prozone effect" or "high-dose hook effect", and is termed "hook effect" in that which follows, results in the measurement signal obtained from samples containing very high concentrations of analyte being found within the standard curve region and these samples being incorrectly assigned an analyte concentrate which is much too low.

It is therefore important to design the single-step immunoassay or the homogeneous sandwich immunoassay in such a way that the limit concentration is shifted as far as possible into the high analyte concentration range or, even better, beyond the naturally occurring analyte concentration range. A further, or alternative, precaution is to introduce a procedural step which registers a hook sample so that the analyte concentration can be determined after the sample has been diluted appropriately.

In connection with a turbidimetric test, Papik et al. proposes achieving this object by using a very elaborate computational method to analyze the reaction kinetics.

EP-A1-0 787 986 proposes using polyclonal antibodies which have been purified by affinity chromatography in such tests. However, this method suffers from the disadvantage that it cannot be applied in all test methods and, in particular, not in non-immunochemical test methods. Further, polyclonal antibodies are not available for all analytes which are to be detected.

U.S. Pat. No. 4,590,169 and U.S. Pat. No. 4,595,661 describe decreasing the hook effect by using antibodies having different affinities. According to U.S. Pat. No. 4,595,661, the sample is incubated with a polystyrene sphere-bound antibody and two horseradish peroxidase-antibody conjugates, with the three antibodies binding to different epitopes on the protein to be detected and the two enzyme-labeled antibodies exhibiting affinities which are markedly different from each other. After the incubation, the unbound substances are removed by washing and the enzyme activity which is bound to the polystyrene sphere is measured. A disadvantage of these methods is that they require antibodies having differing affinities. A further disadvantage is the decrease in the sensitivity of detection in these tests, since the use of conjugates containing low-affinity antibodies results in the background signal being increased because of higher nonspecific binding to the solid phase.

EP-A2-0 617 285 describes a homogeneous turbidimetric hCG test in which, for the purpose of decreasing the hook effect, the sample is first of all incubated with a soluble anti-hCG antibody fragment which possesses at least two binding sites for the analyte; latex particle-bound fragments of anti-hCG antibodies having a different epitope specificity are then added and the change in absorption is measured. The addition of the unlabeled soluble antibody brings about an additional crosslinking of the latex particles and, as a result, a shifting of the hook effect in the direction of higher analyte concentrations. However, homogeneous turbidimetric measurement methods have the disadvantage that they do not exhibit the detection sensitivity which is required for certain parameters.

For the skilled person, therefore, the present invention is directed to developing detection methods, in particular those which exhibit a high degree of detection sensitivity, in such a way that a hook effect is avoided, diminished or at least recognized.

The present invention provides a method for quantitatively or qualitatively detecting an analyte A in a sample, the sample is, for detecting, for avoiding and/or for diminishing the hook effect, incubated with an analyte A-specific binding partner R1, which is associated with a solid phase, an analyte A-specific binding partner R2, which is associated with a label L1, and an analyte A-specific binding partner R3, which is associated with a label L2. The binding partners R2 and R3 are selected such that a saturation of the analyte A-binding sites of the R2 binding partners present in the incubation mixture takes place at a higher analyte A concentration and/or at a later time in the incubation than does the saturation of the analyte A-binding sites of the R3 binding partners which are present in the incubation mixture. The L1-dependent measurement signal is either determined chronologically separated from the L2-dependent or L1 plus L2-dependent measurement signal, or determined using another measurement method. Preference is given to the measurement signal in each case being measured by labels which are associated with the sandwich complexes which have been formed.

The test method according to the invention can be performed independently of the sequence in which R1, R2 and R3 are added or of the respective period of incubation of the sample and the respective binding partner. Unbound reagent components and/or sample constituents can also be removed by a separation or washing step before the measurement signal(s) is/are measured. Such a separation and/or washing step can, for example, also take place after the L1-dependent measurement signal has been measured or before measuring any of the measurement signals.

The measurement signals can in each case be detected, for example, as single measurement values, mean values, medians or sums of several individual measurement values and/or in the form of kinetics. "Different measurement methods" means methods which can detect the L1-dependent measurement signal independently of the L2-dependent or L1 plus L2-dependent measurement signal. For example, label L1 could be a microparticle, which can be measured using a nephelometric method, and label L2 could be an enzyme whose activity is determined photometrically, for example. In another test system, L1 and L2 can be two fluorescent labels whose fluorescence in each case is measured at a different wavelength. For the further analysis, the ratio between the "L1 value" and the "L2 value" or the "L2 plus L1 value" can be calculated, for example, with it being possible for the term "value" to mean the measurement signal directly or a value which has been subject to further revision on the basis of the measurement signal and which is proportional to the measurement signal. The ratio which has been determined in this way can be compared with characteristic values which are specific for the test such that the person who is carrying out the test, or the automated machine, can rapidly recognize whether a hook effect exists and/or whether the sample should be measured once again at a suitable dilution.

The method is based on the formation of the sandwich complexes R1-A-R2 and R1-A-R3 being affected to different extents by the hook effect: a decrease in the measurement signal occurs at a higher sample analyte concentration first in the case of the R1-A-R2 sandwich complex formation than in the case of the R1-A-R3 sandwich complex formation. The skilled person can relatively simply determine the binding partners and reaction conditions which are suitable in each case by first of all measuring the R1-A-R2 sandwich complex formation and the R1-A-R3 sandwich complex formation in separate test methods.

In another embodiment of the invention, binding partners R2 and R3 are the same binding partner. In this case, R2 is employed in the form of R2 aggregates and/or many R2 molecules which are associated with a suspendable solid phase, whereas R3 is employed as a solitary molecule, at least in the initial phase of the incubation.

R2 and R3 can also be different binding partners. For example, it is possible to use, as R2, a binding partner which is directed against a binding site which occurs uniquely on the analyte, whereas R3 recognizes a binding site which occurs several times on the analyte. Furthermore, it is possible to use a binding partner R2 whose ability to bind to the analyte is less pronounced than that of the binding partner R3.

As a rule, the detection sensitivity, a measure of the smallest analyte concentration which can still be detected with confidence, of the test system solid phase R1 and label R2 will be lower than the detection sensitivity of the test system solid phase R1 and label R3. However, the test system solid phase R1 and label R2 will indicate correct concentration values, even at a relatively high analyte concentration. In other words, the test system "solid phase R1 and label R2" covers the upper measurement range better and the test system "solid phase R1 and label R3" covers the lower measurement range better. By detecting the L1 measurement signal, which is proportional to the formation of the R1-A-R2 complex, separately from the L2-dependent or L1 plus L2-dependent measurement signal, it is possible to broaden the measurement range of the test method according to the invention and/or to recognize a hook effect. For example, if the L1 measurement signal is higher than the highest value on the standard curve and the L2 measurement signal is within the standard curve, also termed calibration curve, that is then a sure sign of a "high-dose hook sample". When a hook effect is detected, the sample is tested once again at an appropriate dilution and the correct analyte concentration is determined.

In contrast to the previously known methods, the method according to the invention is also widely applicable over and above the sphere of the immunoassay, e.g., in binding tests using nucleic acid molecules as specific binding partners. The method according to the invention does not require either antibodies which are specially purified or antibodies having different affinities. On the contrary, in a preferred variant of the method according to the invention, R2 and R3 are the same specific binding partner. Furthermore, the method according to the invention can more readily be automated.

Another advantage of the method according to the invention is the possibility of broadening the measurement range: thus, the L1-dependent measurement signal can be used, for example, to determine the concentrations of samples having higher concentrations whereas the L2-dependent measurement signal is used to determine the concentrations of samples having lower concentrations. As a consequence, fewer samples have to be diluted.

By appropriately selecting L1 and L2 and/or the other method parameters, for example the concentration of R2 and/or R3 in the incubation mixture, it is possible to optimize the method according to the invention such that, despite the large measurement range and the reliable detection of the hook effect, the nonspecific binding of R2-L1 to the solid phase has no effect on the test sensitivity which is ensured by way of the R1-solid phase and R3-L2 system.

The method according to the invention can also be used particularly advantageously in the case of analytes which, because of analytes crossreacting with the specific binding partners, can only be determined with very great difficulty using a homogeneous sandwich assay and/or a single-step sandwich assay. Thus, it is customary to determine LH (luteinizing hormone) using an immunoassay which employs antibodies against the α-chain and antibodies against the LH-specific part of the β-chain. If hCG happens to be present in large quantity in the sample, this can result, in the case of a single-step sandwich test and/or a homogeneous test, in all, or almost all, binding sites of the antibodies directed against the α-chain being blocked with hCG molecules. As a consequence, the antibody-LH-antibody sandwich complex cannot form and the concentration of LH in the sample is ascertained incorrectly. Using the method according to the invention, it is now possible to measure such analytes using the much faster single-step sandwich test rather than, as is customary, using a two-step sandwich test: in this case, R1 is selected such that this binding partner recognizes the analyte and the crossreacting substances equally well and R2 and R3 in each case specifically recognize either the analyte or the crossreacting substances. In order to continue with the above-described example for the purpose of illustrating the invention, use will be made, for example, according to the invention, of antibodies directed against the α-chain as R1, of specific anti-hCG antibodies as R2 and of specific anti-LH antibodies as R3. The L1 signal, which is dependent on the formation of the R1-hCG-R2 sandwich, indicates whether, for correctly determining the concentration of LH, the sample does or does not have to be measured once again, for example in a two-step immunoassay. This method according to the invention can also be used, in a corresponding manner, for measuring antibodies, in particular for measuring antibodies belonging to a particular immunoglobulin class, such as IgM, which are directed against a particular, for example viral or bacterial, antigen, with it being possible for the other antibodies which are present in the sample to be present in large excess. This above-described use of the method according to the invention is intended to be included, within the meaning of the invention, in the expression "for detecting, for avoiding and/or for diminishing the hook effect".

Before the invention is explained in further detail, some terms will be clarified in order to facilitate comprehension of the invention:

In a "quantitative detection", the quantity or concentration of the analyte in the sample is measured. The term "quantitative detection" also encompasses semiquantitative methods which only detect the approximate quantity or concentration of the analyte in the sample or can only be used for providing a relative quantity or concentration value. A "qualitative detection" is to be understood as meaning detecting whether the analyte is at all present in the sample, or is absent from it, or indicating that the concentration of the analyte in the sample is below or above a given threshold value or several given threshold values.

The term "analyte" is to be understood as meaning the substance which is to be detected in the test method. Examples of an analyte are listed in EP-A2-0 515 194 on pages 8-15. The analyte can be a member of a specific binding pair. The analyte may possess one binding site (monovalent, normally a hapten) or several binding sites (polyvalent). In immunochemical tests, such a binding site is frequently also designated as an epitope. Furthermore, the analyte can be a single substance or else a group of substances which possess at least one single binding site in common.

A monovalent analyte normally has a molecular weight of from about 100 to 2000, in particular of from about 125 to 1000. Many oligopeptides, oligonucleotides, oligosaccharides, pharmaceuticals, drugs, metabolites, pesticides, etc., are encompassed by the term "a monovalent analyte". A polyvalent analyte normally has a molecular weight of more than about 5000, usually more than about 10,000. Examples of polyvalent analytes are polypeptides, polysaccharides, nucleic acids, cells, cell constituents, including chromosomes, genes, mitochondria and other cell organelles, cell membranes, etc. The substances to be detected are frequently proteins. Such proteins may be members of a protein family whose members are characterized by similar structural features and/or by a similar biological function. Examples of analytically interesting protein families are proteins derived from pathogens, immunoglobulins, cytokines, enzymes, hormones, tumor markers, metabolism markers, tissue-specific antigens, histones, albumins, globulins, scleroproteins, phosphoproteins, mucines, chromoproteins, lipoproteins, nucleoproteins, glycoproteins, proteoglycans, receptors, HLA, coagulation factors, cardiac infarction markers, etc. Examples of other analytically interesting substances are single-stranded and double-stranded oligonucleotides and polynucleotides.

Within the meaning of the invention, a "sample" is to be understood as being the material which is presumed to contain the substance ("analyte") which is to be detected. The term sample encompasses, for example, biological fluids or tissues, in particular derived from humans and animals, such as blood, plasma, serum, sputum, exudate, bronchoalveolar lavage, lymph fluid, synovial fluid, seminal fluid, vaginal mucus, feces, urine, spinal fluid, hair, skin and tissue samples or sections. It also encompasses cell culture samples, vegetable fluids or tissues, forensic samples, water and effluent samples, foodstuffs and pharmaceuticals. The samples may have to be pretreated in order to make the analyte accessible for the detection method or in order to remove interfering constituents in the sample. Such sample pretreatment may involve separating off and/or lysing cells, precipitating, hydrolyzing or denaturing sample constituents, such as proteins, centrifuging samples, treating the sample with organic solvents, such as alcohols, in particular methanol, or treating the sample with detergent. Frequently, the sample is transferred into another, usually aqueous, medium which is intended to interfere as little as possible with the detection method. The analyte may also be amplified. For example, an amplification of nucleic acids leads to the generation of one or more copies of the nucleic acid chain to be detected. Such amplification methods are well known to the skilled person, e.g., "polymerase chain reaction" (PCR), "ligase chain reaction" (LCR), "amplification using Q beta replicase", "nucleic acid sequence-based amplification" (NASBA), "single primer amplification" (ASPP), and others.

A "specific binding partner" is to be understood as being a member of a specific binding pair. The members of a specific binding pair are two molecules which in each case possess at least one structure which is complementary to a structure possessed by the other molecule, with the two molecules being able to bind to each other by means of the complementary structures binding to each other. The term molecule also encompasses molecular complexes, such as enzymes which are composed of an apo enzyme and a coenzyme, proteins which are composed of several subunits, lipoproteins which are composed of protein and lipids, etc. Specific binding partners can be naturally occurring substances or else, for example, substances which are prepared by means of chemical synthesis or using microbiological techniques and/or recombinant methods. Thus, specific binding partners can now be selected with the aid of phage display libraries, by way of synthetic peptide databases or using "recombinatorial antibody libraries" (Larrick & Fry (1991) Human Antibodies and Hybridomas, 2:172-189). In order to illustrate the term specific binding partner, but not to be understood as being a restriction, the following may be mentioned by way of example: thyroxin-binding globulin, steroid-binding proteins, antibodies, antigens, haptens, enzymes, lectins, nucleic acids, repressors, oligonucleotides and polynucleotides, protein A, protein G, avidin, streptavidin, biotin, complement component C1q, nucleic acid-binding proteins, etc. Examples of specific binding pairs are: antibody/antigen, antibody/hapten, operator/repressor, nuclease/nucleotide, biotin/avidin, lectin/polysaccharide, steroid/steroid-binding protein, active compound/active compound receptor, hormone/hormone receptor, enzyme/substrate, IgG/protein A, complementary oligonucleotides or polynucleotides, etc.

Within the meaning of this invention, the term "anti-body" is to be understood as being an immunoglobulin, e.g., an immunoglobulin of the IgA, IgD, IgE, $IgG_1$, $IgG_2a$, $IgG_2b$, $IgG_3$, $IgG_4$ and IgM class or subclass. An antibody possesses at least one binding site (frequently termed a paratope) for an epitope (frequently also termed antigen determinant) on an antigen or hapten. Such an epitope is characterized, for example, by its spatial structure and/or by the presence of polar and/or apolar groups. The binding site belonging to the antibody is complementary to the epitope. The antigen-antibody reaction, or the hapten-antibody reaction, functions in accordance with what is termed the "key-keyhole principle" and is as a rule very highly specific, i.e., the antibodies are able to distinguish between small differences in the primary structure, in the charge, in the spatial configuration and in the steric alignment of the antigen or hapten. What are termed the "complementarity-determining regions" of the antibody make a particular contribution to the binding of the antibody to the antigen or hapten.

The term "antigens" encompasses monovalent and polyvalent antigens. A polyvalent antigen is a molecule or a molecular complex to which more than one immunoglobulin is able to bind simultaneously, whereas in each case only one single antibody can bind at a given time in the case of a monovalent antigen. A hapten is normally the name given to a molecule which is not immunogenic on its own and which, for immunization purposes, is normally bound to a carrier.

Within the meaning of this invention, the term "antibody" is to be understood as meaning not only complete antibodies but also, expressly, antibody fragments, such as Fab, Fv, F(ab')$_2$ and Fab'; and also, in addition, chimeric, humanized, bispecific, oligo-specific or "single-chain" antibodies; and, in addition, aggregates, polymers and conjugates of immunoglobulins and/or their fragments, providing the properties of binding to the antigen or hapten are retained. Antibody fragments can be prepared, for example, by enzymically cleaving antibodies with enzymes such as pepsin or papain. Antibody aggregates, antibody polymers and antibody conjugates can be generated using a wide variety of methods, for example by means of heat treatment, by reacting with substances such as glutaraldehyde, by reacting with immunoglobulin-binding molecules, by biotinylating antibodies and subsequently reacting with streptavidin or avidin, etc.

Within the meaning of this invention, an antibody can be a monoclonal antibody or a polyclonal antibody. The antibody may be prepared by means of customary methods, for example by immunizing humans or an animal, such as a mouse, rat, guinea pig, rabbit, camel, horse, sheep, goat or chicken (see also Messerschmid (1996) BIOforum, 11:500-502), and subsequently isolating the antiserum; or by means of establishing hybridoma cells and subsequently purifying the secreted antibodies; or by means of cloning and expressing the nucleotide sequences, or modified versions thereof, which encode the amino acid sequences which are responsible for binding the natural antibody to the antigen and/or hapten. Where appropriate, recombinant methods can also be used to prepare antibodies in plant cells, such as yeast cells (Fischer et al. (1999) Biol. Chem., 380:825-839; Hiatt et al. (1992) Genetic Engineering, 14:49-64)), animal cells and procaryotic cells (see, e.g., WO 95/25172), and also isolated human cells.

Within the meaning of this invention, the term "solid phase" encompasses an object which is composed of porous and/or nonporous, as a rule water-insoluble, material and which can have a very wide variety of shapes, for example vessel, tube, microtitration plate, sphere, microparticle, rod, strip, filter paper or chromatography paper, etc. As a rule, the surface of the solid phase is hydrophilic, or can be made hydrophilic. The solid phase can be composed of a very wide variety of materials, such as inorganic and/or organic materials, synthetic materials, naturally occurring materials and/or modified naturally occurring materials. Examples of solid phase materials are polymers, such as cellulose, nitrocellulose, cellulose acetate, polyvinyl chloride, polyacrylamide, crosslinked dextran molecules, agarose, polystyrene, polyethylene, polypropylene, polymethacrylate and nylon; ceramics; glass; metals, in particular precious metals such as gold and silver; magnetite; mixtures and combinations thereof; etc. The term solid phase also includes cells, liposomes and phospholipid vesicles.

The solid phase can possess a coating composed of one or more layers, for example composed of proteins, carbohydrates, lipophilic substances, biopolymers or organic polymers, or mixtures thereof, in order, for example, to suppress or prevent the nonspecific binding of sample constituents to the solid phase or, for example, in order to achieve improvements with regard to the stability of particulate solid phases in suspension, or with regard to storage stability, formative stability or resistance to UV light, microbes or other agents having a destructive effect.

The term "associated" is to be understood broadly and encompasses, for example, a covalent and a noncovalent bond, a direct and an indirect linkage, adsorption to a surface and inclusion in a recess or a cavity, etc. In the case of a covalent bond, the antibodies or binding partners are bonded to the solid phase or the label by way of a chemical bond. Normally, a covalent bond is considered to exist between two molecules when at least one atomic nucleus in one of the molecules shares electrons with at least one atomic nucleus in the second molecule. Examples of a noncovalent bond are surface adsorption, inclusion in cavities or the binding of two specific binding partners. In addition to a direct linkage to the solid phase or the label, the antibodies or binding partners can also be bound to the solid phase or the label indirectly by way of specific interaction with other specific binding partners (see also EP-A2-0 411 945). This will be illustrated in more detail with the aid of examples: the biotinylated antibody can be bound to the label by way of label-bound avidin; or a fluorescein-antibody conjugate can be bound to the solid phase by way of solid phase-bound anti-fluorescein antibodies; or the antibody can be bound to the solid phase or the label by way of immunoglobulin-binding proteins.

A "signal-forming system" can have one or more components, with at least one component being a detectable label. A label is to be understood as being any molecule which itself produces a signal or which is able to induce the production of a signal, such as a fluorescent substance, a radioactive substance, an enzyme or a chemiluminescent substance. The signal can be detected or measured with the aid, for example, of the enzyme activity, the luminescence, the light absorption, the light scattering, the emitted electromagnetic or radioactivity radiation, or a chemical reaction.

A "label" is itself able to generate a detectable signal such that no further components are necessary. Many organic molecules absorb ultraviolet and visible light, with these molecules being able to pass into an excited energy state, as a result of the energy transferred by the light absorption, and emitting the absorbed energy in the form of light at a wavelength which is different from that of the incident light. Other labels, in turn, such as radioactive isotopes, dyes and magnetic and nonmagnetic microparticles, are able to generate a detectable signal directly.

Yet other labels require further components for generating the signal, i.e., in such a case, the signal-producing system includes all the components which are required for forming the signal, such as substrates, coenzymes, quenchers, accelerators, additional enzymes, substances which react with enzyme products, catalysts, activators, cofactors, inhibitors, ions, etc.

Examples of suitable labels (see also EP-A2-0 515 194; U.S. Pat. No. 5,340,716; U.S. Pat. No. 5,545,834; Bailey et al. (1987) J. Pharmaceutical & Biomedical Analysis 5:649-658) are enzymes, including horseradish peroxidase, alkali phosphatase, glucose-6-phosphate dehydrogenase, alcohol dehydrogenase, glucose oxidase, β-galactosidase, luciferase, urease and acetyl cholinesterase; dyes; fluorescent substances, including fluorescein isothiocyanate, rhodamine, phycoerythrin, phycocyanin, ethidium bromide, 5-dimethylaminonaphthalene-1-sulfonyl chloride and fluorescent chelates of rare earths; chemiluminescent substances, including luminol, isoluminol, acridium compounds, olefin, enol ether, enamine, aryl vinyl ether, dioxene, arylimidazole, lucigenin, luciferin and aequorin; sensitizers, including eosin, 9,10-dibromoanthracene, methylene blue, porphyrin, phthalocyanin, chlorophyll, Rose Bengal; coenzymes; enzyme substrates; radioactive isotopes, including $^{125}$I, $^{131}$I, $^{14}$C, $^{3}$H, $^{32}$P, $^{35}$S, $^{14}$C, $^{51}$Cr, $^{59}$Fe, $^{57}$Co and $^{75}$Se; particles, including magnetic particles or particles, preferably latex particles, which can themselves be labeled, for example, with dyes, sensitizers, fluorescent substances, chemiluminescent substances, isotopes or other detectable labels; sol particles, including gold and silver sols; liposomes and cells which can themselves be labeled with detectable labels; etc.

A signal-forming system can also encompass components which, being in spatial proximity to each other, can enter into a detectable interaction, for example in the form of energy donors and energy recipients, such as photosensitizers and chemiluminescent substances (EP-A2-0 515 194), photosensitizers and fluorophores (WO 95/06877), radioactive iodine$^{125}$ and fluorophores (Udenfriend et al. (1985) Proc. Natl. Acad. Sci. 82:8672-8676), fluorophores and fluorophores (Mathis (1993) Clin. Chem. 39:1953-1959) or fluorophores and fluorescence quenchers (U.S. Pat. No. 3,996,345).

An interaction between the components includes the direct transfer of energy between the components, for example by means of light or electron radiation, and also by way of short-lived reactive chemical molecules. Furthermore, this term also encompasses processes in which the activity of a component is inhibited or reinforced by one or more other components, for example the inhibition or enhancement of the enzyme activity, or the inhibition, enhancement or change (e.g., wavelength shift, polarization) of the electromagnetic radiation which is emitted by the affected component. The interaction between the components also encompasses enzyme cascades. In this case, the components are enzymes, at least one of which supplies the substrate for another enzyme, resulting in a maximum or minimum reaction rate of the coupled substrate conversion.

As a rule, an effective interaction between the components takes place when these components are spatially adjacent, that is, for example, within a distance range of a few in particular within a distance range of less than about 600 nm, preferably less than about 400 nm, very particularly preferably of less than about 200 nm.

Microparticles are frequently used as the solid phase and/or the label. Within the meaning of this invention, the term "microparticles" is to be understood as meaning particles which have an approximate diameter of at least about 20 nm and not more than about 20 μm, usually between about 40 nm and about 10 μm, preferably between about 0.1 and about 10 μm, particularly preferably between about 0.1 and about 5 and very particularly preferably between about 0.15 and about 2 μm. The microparticles may have a regular or irregular shape. They can be spheres, spheroids, spheres containing cavities of different sizes, or pores. The microparticles can be composed of organic material or inorganic material, or of a mixture or combination of the two types of material. They can be composed of a porous or nonporous material, or of a swellable or non-swellable material. While the microparticles can in principle have any density, preference is given to particles having a density which approaches the density of water, such as from about 0.7 to about 1.5 g/ml. The microparticles can be suspended in aqueous solutions and are stable in suspension for as long a time as possible. They may be transparent, partially transparent or opaque. The microparticles can be composed of several layers, such as what are termed the "core-and-shell" particles, which have a core and one or more enveloping layers. The term microparticles encompasses, for example, dye crystals, metal sols, silica particles, glass particles, magnetic particles, polymer particles, oil drops, lipid particles, dextran and protein aggregates. Preferred microparticles are particles which can be suspended in aqueous solutions and which are composed of water-insoluble polymeric material, in particular of substituted polyethylenes. Latex particles, for example composed of polystyrene, acrylic acid polymers, methacrylic acid polymers, acrylonitrile polymers, acrylonitrile-butadiene-styrene, polyvinyl acetate-acrylate, polyvinylpyridine or vinyl chloride-acrylate are of interest. Latex particles which possess reactive groups, such as carboxyl, amino or aldehyde groups, on their surface, which groups enable specific binding partners, for example, to bind covalently to the latex particles, are of interest. The preparation of latex particles is described, for example, in EP 0 080 614, EP 0 227 054 and EP 0 246 446.

Preference is given to the method according to the invention being a heterogeneous or homogeneous binding test in accordance with the sandwich format.

In "homogeneous binding tests", no separation takes place between free and complex-bound analytes. Many turbidimetric or nephelometric methods represent examples of homogeneous immunoassays (see also Boguslaski & Li (1982) Applied Biochemistry and Biotechnology, 7:401-414) with it being possible for the specific binding partners employed for the detection in these methods to be associated with latex particles; EMIT® tests; CEDIA® tests; fluorescence polarization immunoassays; luminescent oxygen channeling immunoassays (EP-A2-0 515 194; Ullman et al. (1994) Proc. Natl. Acad. Sci., 91:5426-5430; Ullman et al. (1996) Clinical Chemistry, 42:1518-1526); etc. In what are termed the gene probe tests, the specific binding partners are as a rule nucleic acid chains which are at least partially complementary to sections of the nucleic acid chain to be detected.

"Heterogeneous binding tests" are characterized by one or more separation steps and/or washing steps. The separation can be effected, for example, by immune precipitation, precipitation with substances such as polyethylene glycol or ammonium sulfate, filtration, magnetic separation or binding to a solid phase, such as to a tube, a sphere, a microtitration plate well or a filter paper or chromatography paper.

In "heterogeneous binding tests in accordance with the sandwich format", the analyte is normally bound by a solid phase-associated specific binding partner and a specific binding partner which is associated with a component of a signal-forming system. In this connection, the specific binding partners can be different or identical, for example, in a sandwich immunoassay, an analyte-specific monoclonal antibody can be employed both as the catching agent (e.g. as the solid phase antibody) and as the labeled antibody, if the analyte possesses more than one epitope for this antibody. In the case of a sandwich immunoassay, the specific binding partners can be analyte-specific antibodies or, if the analyte itself is an antibody, the antigen and/or a "modified antigen", for example a labeled antigen, an antigen fragment or an antigen analog. Examples of such sandwich complexes are: solid phase-antibody◇analyte◇antibody-label or solid phase-antigen◇analyte (=antibody)◇antigen-label.

Within the meaning of this invention, the "indirect immunoassay" is a special embodiment of a heterogeneous immunoassay: in this case, the analyte is an antibody. One of the specific binding partners is its antigen and/or a modified antigen, and the other specific binding partner is as a rule an antibody which binds the analyte and/or an immunoglobulin-binding protein. Examples of such complexes, which can be formed in an indirect immunoassay, are: solid phase-anti- IgM antibody⇔analyte (=anti-HbsAg IgM)⇔HbsAg-label or solid phase-HbsAg⇔analyte (=anti-HbsAg IgG)⇔protein A-label.

The above-described sandwich tests, including the indirect immunoassays, can also be carried out as homogeneous test methods (see also EP-A2-0 515 194).

A preferred embodiment of the method according to the invention is one in which (i) the sample is incubated with an analyte A-specific binding partner R1, which is associated with a solid phase, an analyte A-specific binding partner R2, which is associated with a label L1, and an analyte A-specific binding partner R3, which is associated with a member X of a specific binding pair; (ii) at a later time, label L2, which is associated with the binding pair member Y, corresponding to X, of a specific binding pair, is added to the test mixture; and (iii) the measurement signal is determined at at least two times T1 and T2, with the earlier time T1 being at the latest shortly after adding label L2, which is associated with binding pair member Y, and the later time T2 being after adding label L2, which is associated with binding pair member Y.

The period of time defined by the phrase "shortly after adding label L2" is to be understood in such a way that the period "addition of label L2 to measurement of L1" is short as compared with the period "addition of label L2 to measurement of label L2", i.e., preferably less than about 30%, particularly preferably less than about 15%, of the period "addition of label L2 to measurement of label L2".

In a particularly preferred method, the time T1 is before adding label L2.

Another preferred method according to the invention is one in which (i) the sample is incubated with an analyte A-specific binding partner R1, which is associated with a solid phase, an analyte A-specific binding partner R2, which is associated with a label L1, and an analyte A-specific binding partner R3, which is associated with a member X of a specific binding pair; (ii) at a later time, label L2, which is associated with the binding pair member Y, which corresponds to X, of a specific binding pair, is added to the test mixture; and (iii) the measurement signal of L1 and the measurement signal of L2 are determined using different measurement methods.

The label L1 could, for example, be a microparticle and the label L2 could be a fluorescent or chemiluminescent label, such that the measurement signal L1 could be determined turbidimetrically or nephelometrically and the measurement signal of L2 could be determined using a fluorimeter or instrument for measuring chemiluminescence. In another embodiment according to the invention, L1 and L2 could, for example, be different fluorescent labels whose fluorescent light is in each case detected at a different wavelength.

Binding pairs X⇔Y for the above-described methods are, in particular, biotin⇔avidin, biotin⇔streptavidin, or hapten⇔anti-hapten antibodies, such as fluorescein⇔anti-fluorescein, digoxin⇔anti-digoxin, or antigen⇔anti-antigen antibody, such as peroxidase⇔anti-peroxidase, or nucleic acid pairs.

Another embodiment according to the invention is a test based on the LOCI™ method. In this case, the sample is incubated with an analyte A-specific binding partner R1, which is associated with a sensitizer particle, an analyte A-specific binding partner R2, which is associated with a chemiluminescer particle, and an analyte A-specific binding partner R3, which is associated with a member X of a specific binding pair, preferably biotin; (ii) at a later time, chemiluminescer particles, which are associated with the binding pair members Y, which correspond to X, preferably streptavidin and/or avidin, of a specific binding pair, are added to the test mixture; and (iii) the measurement signal is determined at at least two times T1 and T2, with the earlier time T1 being at the latest shortly after adding the chemiluminescer particles, which are associated with binding pair members Y, and the later time T2 being after adding chemiluminescer particles which are associated with binding pair members Y. The sensitizer molecules which are associated with the sensitizer particle can generate singlet oxygen when they are in the excited state. This singlet oxygen can react with the chemiluminescent compounds which are associated with the chemiluminescer particles, with the metastable compound which is formed decomposing once again with the production of a light flash. Since singlet oxygen is only stable in aqueous solutions for a short time, the only chemiluminescer particles to be excited to emit light are those which, for example as a result of immune complex formation, are in the immediate vicinity of the sensitizer particles which have been excited, for example by means of light. The wavelength of the emitted light which is to be measured can be changed by using appropriate fluorescent dyes in the chemiluminescer particles. A detailed description of the LOCI™ method can be found, for example, in EP-A2-0 515 194. The LOCI™ method is also discussed in U.S. Pat. No. 6,187,594, which is incorporated by reference herein in its entirety. The term "sensitizer particles" is to be understood as meaning, in particular, microparticles which are labeled with one or more dyes which generate singlet oxygen when irradiated with light. The term "chemiluminescer particles" is to be understood as meaning, in particular, microparticles which contain dyes which react with singlet oxygen while emitting light.

In the methods according to the invention, R1 and R2, R1 and R3, R1, R2 and R3, or R2 and R3, can be the same binding partner; this applies, in particular, when the analyte to be detected possesses at least two identical binding sites. Thus, many bacterial antigens or many tumor markers, for example, possess repetitive epitopes such that several copies of a monoclonal antibody are able to bind to these antigens. In a test method according to the invention for detecting such antigens, such a monoclonal antibody could consequently be employed as binding partner "R1 and R2", "R1 and R3", "R2 and R3" or "R1, R2 and R3". In a particularly preferred embodiment, R2 and R3 are the same binding partner, with R2 preferably having to be associated with a suspendable solid phase.

Furthermore, in the methods according to the invention, L1 and L2 can be the same label, for example chemiluminescer particles. Thus, in such a case, the measurement signal of the chemiluminescer particles could be determined turbidimetrically or nephelometrically as label L1 and the measurement signal of the chemiluminescer particles could be determined as label L2 plus L1 using a luminometer. In another embodiment, the measurement signal of the chemiluminescer particles could be determined as label L1, and the measurement signal of the chemiluminescer particles as label L2 plus L1, in each case at different times using a luminometer.

In a preferred method according to the invention, the solid phase is a suspendable solid phase, preferably microparticles such as latex particles or magnetic particles.

The suspendable solid phase can also function as a label, particularly when it consists of microparticles. Latex particles, magnetic particles and sensitizer particles constitute examples of such a solid phase.

A method according to the invention in which the binding partners R2 are associated with a suspendable solid phase is also preferred, particularly when they are covalently bonded to this phase. In this connection, the suspendable solid phase is, in particular, composed of microparticles, particularly preferably microparticles which constitute the label L1, or, very particularly preferably, composed of chemiluminescer particles.

Another method according to the invention is one in which, as a consequence of the sandwich formation, components of a signal-forming system, which includes label L1 and/or label L2, are brought to a distance from each other which permits an interaction, in particular an energy transfer, between these components, and the extent of the interaction is measured, e.g., the method, which is described above and in the examples, based on LOCI™ technology.

In a preferred method according to the invention, the signal-forming system encompasses photosensitizers which are associated with microparticles and chemoluminescent substances which are associated with microparticles.

Furthermore, the invention encompasses the use of an analyte A-specific binding partner R1, which is associated with a solid phase, an analyte A-specific binding partner R2, which is associated with a label L1, and an analyte A-specific binding partner R3, which is associated with a label L2, for detecting, avoiding and/or decreasing the hook effect in a method, in particular a homogeneous sandwich test, for quantitatively or qualitatively detecting an analyte A in a sample. In this connection, the saturation of the analyte A-binding sites of the binding partners R2 which are present in the incubation mixture takes place at a higher analyte A concentration and/or at a later time in the incubation than does the saturation of the analyte A-binding sites of the binding partners R3 which are present in the incubation mixture, and the L1-dependent measurement signal is either determined at a different time from the L2-dependent or L1 plus L2-dependent measurement signal or is determined using a different measurement method.

The invention also covers the use of an analyte A-specific binding partner R1, which is associated with a solid phase, an analyte A-specific binding partner R2, which is associated with a label L1, an analyte A-specific binding partner R3, which is associated with a member X of a specific binding pair, and a label L2, which is associated with the binding pair member Y, corresponding to X, of a specific binding pair, for detecting, avoiding and/or decreasing the hook effect in a method, in particular in a homogeneous sandwich test, for quantitatively or qualitatively detecting an analyte A in a sample. The saturation of the analyte A-binding sites of the binding partners R2 which are present in the incubation mixture takes place at a higher analyte A concentration and/or at a later time in the incubation than does the saturation of the analyte A-binding sites of the binding partners R3 which are present in the incubation mixture.

Another part of the subject-matter of the invention is a test kit for a heterogeneous or homogeneous sandwich test for quantitatively or qualitatively detecting an analyte A in a sample, which kit contains an analyte A-specific binding partner R1, which is associated with a solid phase, an analyte A-specific binding partner R2, which is associated with a label L1, and an analyte A-specific binding partner R3, which is associated with a label L2, preferably in separate receptacles, and with the saturation of the analyte A-binding sites of the binding partners R2 which are present in the incubation mixture taking place, in the sandwich test, at a higher analyte A concentration and/or at a later time in the incubation than does the saturation of the analyte A-binding sites of the binding partners R3 which are present in the incubation mixture.

Another test kit according to the invention for a heterogeneous or homogeneous sandwich test for quantitatively or qualitatively detecting an analyte A in a sample contains an analyte A-specific binding partner R1, which is associated with a solid phase, an analyte A-specific binding partner R2, which is associated with a label L1, an analyte A-specific binding partner R3, which is associated with a member X of a specific binding pair, and a label L2, which is associated with the binding pair member Y, corresponding to X, of a specific binding pair, preferably in separate receptacles, and with the saturation of the analyte A-binding sites of the binding partners R2 which are present in the incubation mixture taking place, in the sandwich test, at a higher analyte A concentration and/or at a later time in the incubation than does the saturation of the analyte A-binding sites of the binding partners R3 which are present in the incubation mixture. Particular preference is given to such a test kit in which the analyte A-specific binding partner R2, which is associated with a label L1, and the analyte A-specific binding partner R3, which is associated with a member X of a specific binding pair, are present together in one receptacle.

Furthermore, the invention relates to test kits which contain the components which are required for implementing the method according to the invention.

Test kits according to the invention can also contain an information leaflet, dilution buffer, standards, controls, system reagents and/or other components which are required for carrying out the test. Particularly preferred test kits according to the invention contain an information leaflet which describes the method according to the invention.

FIG. 1 shows a diagram of a preferred test method according to the invention ("S"=solid phase). In a first step, solid phase-R1, analyte ("A"; provided it is present in the sample), R2-L1 and R3-L2 (or R3-X) are mixed together and this incubation mixture is incubated until time T1. At time T1, the measurement signal of the label L1 which is contained in the binding complex solid phase-R1-analyte-R2-L1 is determined. After that, Y-L2 (only in the case of R3-X) is added and the incubation mixture is incubated until time T2. After that, i.e. at time T2, the measurement signal of the label L2 which is present in the binding complex solid phase-R1-analyte-R3-L2 (or -R3-X-Y-L21 is determined. If L1 and L2 are the same labels, preference is given to determining the measurement signal of both the labels L1 and L2 which are present in the binding complexes at time T2. Instead of measuring the measurement signal of the bound labels, it is also possible, in each case or alternatively, to measure the measurement signal of the unbound portion of the label, i.e., the label which is not present in the binding complex, in the incubation mixture.

FIG. 2 depicts the determination of high-dose hook samples, with the magnitude of the signal at time T2 being plotted against the "T2 signal/T1 signal value".

The examples which are described below serve to illuminate some aspects of this invention in an exemplary manner and are not to be understood as being a restriction.

EXAMPLES:
Abbreviations employed:

| | |
|---|---|
| ADx | aminodextran |
| Biotin-X-NHS | sulfosuccinimidyl-6-(biotinamido)-hexanoate |
| BSA | bovine serum albumin |
| C-bead-ADx | aminodextran-coated chemiluminescer particles |
| C-bead-ADx-DxAl | aminodextran- and dextranaldehyde-coated chemiluminescer particles |
| CMO | carboxymethyloxime or carboxymethoxyl-amine hemihydrochloride |
| DMAP | 4-dimethylaminopyridine |
| DMF | dimethylformamide |
| DMSO | dimethyl sulfoxide |

EXAMPLES:
Abbreviations employed:

| | |
|---|---|
| DxAl | dextranaldehyde |
| EDAC | 1-ethyl-3-(dimethylpropyl)carbodiimide |
| MES | 2-(N-morpholino)ethanesulfonic acid |
| MOPS | 3-N- (morpholino) propanesulfonic acid |
| NaBH$_3$CN | sodium cyanoborohydride |
| NaHCO$_3$ | sodium hydrogen carbonate |
| NaOH | sodium hydroxide |
| NH$_2$ | amino group |
| Sulfo-SMCC | sulfosuccinimidyl-4-(maleimidomethyl)-cyclohexane-1-carboxylate |
| SC-ADx | single-coated amidodextran |
| S-bead-ADx | aminodextran-coated sensitizer particles |
| S-bead-DxAl | dextranaldehyde-coated sensitizer particles |
| S-bead-DxAl-SAV | streptavidin-coated onto S-bead-DxAl |
| STUT | O-(N-succinimidyl)-N,N,N'-tetramethyl-uronium tetrafluoroborate |
| TAPS | 3-[N-tris-(hydroxymethyl)methylamino]-propanesulfonic acid sodium salt |
| TAR | thioxene, anthracene, rubrene |
| Tris | tris(hydroxymethyl)aminomethane |
| Zn (BF$_4$)$_2$ | zinc fluoroborate |

EXAMPLE 1

Staining the Latex Particles

1) Chemiluminescer Particles

Latex particles (Seradyn, Catalog No.: 83000550100890; diameter of approx. 0.2 µm) are suspended in a mixture composed of ethylene glycol, 2-methoxyethanol and NaOH (65.4%, 32.2% and 2.3%) and stirred at 95° C.±3° C. for 40 minutes. Thioxene (203 mg/g of particles), 1-chloro-9,10-bis (phenylethynyl)anthracene (16 mg/g of particles) and rubrene (27 mg/g of particles) are incubated at 95° C.±3° C. for 30 minutes in a 2-ethoxy-ethanol solution. The two mixtures are combined and incubated for a further 20 minutes while being stirred. After the 20 minutes, the particle suspension is cooled down to 40° C.±10° C. The stained particles are passed through a 43 micron mesh polyester filter and washed (Microgen Lab System). The particles are first of all washed with a solvent mixture composed of ethylene glycol and 2-ethoxyethanol (70% and 30%, 500 ml per gram of particle) and then with 10% ethanol (pH 10-11, 400 ml per gram of particles).

2) Sensitizer Particles

Latex particles (Seradyn, catalog No. 83000550100890; diameter approx. 0.2 µm) are suspended in a solvent mixture composed of 2-ethoxyethanol, ethylene glycol and NaOH (65.4%, 32.2% and 2.3%) and stirred at 95° C.±3° C. for 40 minutes. The sensitizer dye (t-butyl silicone phthalocyanine) is dissolved in benzyl alcohol (92 g of dye/5 ml/g of particles) and heated at 95° C. 3° C. for 30 minutes. After the two incubation times have come to an end, the mixtures are combined and stirred for a further 20 minutes. The particle suspension is cooled down to 40° C.±10° C. and filtered through a 43 micron mesh polyester filter and then washed. The particles are first of all washed with ethyl alcohol (700 ml per gram of particles) and subsequently with 10% ethanol (pH 10-11, 600 ml per gram of particles).

EXAMPLE 2

Preparing Aminodextran (ADx)

Several methods for preparing aminodextran are known. One method will be presented here. Hydropropyldextran (1 NH$_2$/7 glucose) is prepared by dissolving dextran T-500 (Pharmacia, Uppsala, Sweden; 50 g) in 150 ml of water in a spherical glass receiver fitted with a stirrer and a dropping funnel. 18.8 g of Zn(BF$_4$)$_2$ are added to the solution, which is then brought to a temperature of 87° C. using a water bath. Epichlorohydrin (350 ml) is added dropwise to the solution, while stirring, within the space of 30 minutes. The mixture is stirred at 85° C. to 95° C. for a further 4 hours and then cooled down to room temperature. The resulting chlorodextrin is precipitated, by adding the solution to 3 l of methanol, while stirring, and, after that, filtered and dried overnight in a vacuum oven.

The chlorodextran is dissolved in 200 ml of water and this solution is added to 2 liters of 36% ammonia. The solution is stirred at room temperature for 4 days and then concentrated down to 190 ml in a rotary evaporator. The concentrate is divided into two equal parts and in each case slowly added to 2 liters of methanol. The precipitate is filtered off and dried in a vacuum oven.

The dried precipitate is dissolved in 50 mM MOPS, pH 7.2 (12.5 mg/ml). The solution is stirred at room temperature for 8 hours, then cooled (4-8° C.) and centrifuged at 15,000 rpm for 45 minutes in a Sorvall RC-5B centrifuge. 23.1 g of Sulfo-SMCC in 1 ml of water are added to 10 ml of the supernatant. The mixture is incubated for 1 hour and used, without any further pretreatment, for coating the stained chemiluminescer particles (see Example 4).

EXAMPLE 3

Preparing Dextranaldehyde (DxAl)

Dextranaldehyde is prepared by stirring 400 g of Dextran T-500 (Phamacia, Uppsala, Sweden), at 70° C., in 1.5 liters of water in a 4 liter flask. The solution is filtered, and a Zn(BF$_4$)$_2$ solution (400 ml, 25% by weight in water, pH 1.8) is added under argon. Allyl-2,3-epoxypropylether is added in portions (3×500 ml, 8-10 ml/min) at a temperature of 70° C. The solution is stirred at 80° C. and under argon for a further 12-13 hours. After that, the reaction mixture is cooled down and added to 6 liters of water. The dilute mixture is subjected to ultrafiltration using a Microgen tangential flow diafiltration system and concentrated down to 1.0-1.5 liters.

The allyloxydextran is then ozonylated while stirring. The ozone is generated using an ozonizer and bubbled through the allyloxydextran solution under pressure (9.0 psi) at a flow rate of 2 liters per minute. 10 ml of heptanol are added as an anti-foaming agent. After approx. 10 hours, the solution is cooled down to 10° C. 50 ml of dimethyl sulfide are added under argon. After 10 hours of continuous stirring, the dextranaldehyde is purified by means of a Microgen Ultrafiltration.

EXAMPLE 4

Preparing Aminodextran-Coated Tar Particles (C-Bead-ADx)

1 ml (22 mg/ml) of the stained chemiluminescer particles (Example 1, paragraph 1) are mixed with 1 ml of an aminodextran solution (20 mg/ml, MW 500K, see Example 2) in 0.05 MES, pH 6.0, in the presence of 3.8 mg of EDAC/ml. After having been incubated at room temperature ("RT") in the dark for 16 hours, the particles are washed with 2 ml of 0.05 M MES and, after that, with 6 ml of 0.05 M MES (1 M NaCl, pH 6.0). The particles are taken up in 1 ml of 0.05 M MES, pH 6.0 (22 mg of SC-ADx particles/ml). The particles are washed by being centrifuged (Sorval RC-5 B Plus or Eppendorf 5415C centrifuge) and resuspended by means of sonication (Branson Sonifier-450).

EXAMPLE 5

Coating the C-bead-ADx with Dextranaldehyde 1 ml of a dextranaldehyde solution (20 mg/ml, see Example 3, MW 500K) and 1 ml of a 22 mg of C-bead-ADx/ml solution (0.05 M MES, pH 6) are incubated together with 2 mg of $NaBH_3CN$/ml. After having been incubated at 37° C. and in the dark for 20 hours, the particles are washed twice with 5 ml of MES buffer. The particles are then suspended in 0.5 ml of 0.05 M MES, 0.4% Tween 20, pH 6 (40 mg of C-bead-ADx-DxAl/ml).

EXAMPLE 6

Coating the c-Bead-ADx-DxAl with Anti-Human IgG Antibodies

Antibody-coated particles are prepared by mixing equal volumes of an antibody solution (20 mg of anti-human IgG antibody/ml in 0.05 M MES, pH 5.0) and a particle suspension (40 mg of C-bead-ADx-DxAl/ml in 0.05 M MES, 0.4% Tween-20, pH 6) in the presence of 0.5 mg $NaBH_3CN$/ml. After incubating at room temperature for 16 hours, the remaining aldehyde groups are reacted with 0.08 M CMO (carboxymethyl oxime or carboxymethoxylamine) at 37° C. for 90 minutes. The particles are then washed 3-4 times with a suitable buffer (tris buffer, 1% BSA, 0.1% Zwittergent 3-14). After the last resuspension, the concentration of the particles is 1 mg/ml.

EXAMPLE 7

Preparing Dextranaldehyde-Coated Sensitizer Particles (S-Bead-DxAl)

The sensitizer particles from Example 1, paragraph 2, are diluted down to 20 mg/ml in water. They are then adjusted to a concentration of 18 mg/ml with 300 mM TAPS buffer, pH 9.0. Hydrazine (36.3 µl/g of particles), STUT (0.456 g/g of particle) and DMAP (23.2 mg/g of particles) are added. STUT (freshly prepared in DMF, 10%) is added in 4 portions every 15 minutes. DMAP (freshly prepared in DMF, 10%) is added after the first addition of the STUT. After each addition of STUT, the pH is readjusted to 9.0. After stirring at room temperature for one hour, the particles are washed with 10 times their volume of TAPS buffer, pH 9.0 (Microgen system).

The particles are taken up in 1 mM TAPS buffer (20 mg/ml) and this suspension is slowly added, while stirring vigorously, to 40 mg of dextranaldehyde/ml in acetate buffer, pH 5.0. After 30 minutes, the reaction temperature is adjusted to 50° C. and the mixture is incubated for a further 18 hours while being stirred. The particles are then washed with 25 times their volume of water (Microgen system).

EXAMPLE 8

Preparing Streptavidin-Coated Sensitizer Particles (S-Bead-DxAl-SAv)

The dextranaldehyde-coated particles (S-bead-DxAl, 100 mg/ml) are added to a streptavidin solution (30 mg/ml, in 10 mM phosphate buffer, pH 7). The solution is stirred at 37° C. for 1 hour. After that, sodium cyanoborohydride ($NaBH_3CN$ in water, 50 mg/ml, 2% of the total volume) is added while stirring and the total mixture is stirred at 37° C. for a further 40-72 hours. After that, 1 M carboxymethoxylamine (CMO) in acetate buffer, pH 5, is added (1.5% of the total mixture) and the whole is incubated for a further two hours. After that, the particles are washed with 25 times their volume of a protein-free buffer (0.1 M tris, 0.3 M NaCl, 25 mM EDTA, pH 8.2).

EXAMPLE 9

Preparing Rubella Antigen-Coated Sensitizer Particles

In order to prepare rubella antigen-coated sensitizer particles, the dextranaldehyde-coated particles (S-bead-DxAl) are reacted, in a first step, with L-lysine and, in a second step, with succinic anhydride. The rubella antigen is then coupled onto the carboxyl groups.

10 ml of a lysine solution (40 mg/ml in MES, pH 6.0) are added to 10 ml of S-bead-DxAl particles (100 mg/ml in 50 mM MES, 0.2% Tween 20, pH 6.0). 200 µl of a 10% Tween 20 solution are then added. 2 ml of a freshly prepared sodium cyanoborohydride solution (25 mg/ml in $H_2O$) are added. The mixture is incubated at 37° C. for 4 hours. After that, a further 2 ml of a freshly prepared sodium cyanoborohydride solution (25 mg/ml in $H_2O$) are added. The reaction mixture is incubated at 37° C. for a further 16 hours on the roller-type mixer. After that, 10 ml of borate buffer (200 mM, pH 9.0) are added and the mixture is centrifuged for 30 minutes (16,000 rpm, 10° C.) and the supernatant discarded. The pellet is taken up, and resuspended, in 15 ml of borate buffer. This mixture is then sonicated in a water bath using a Sonifier 250 (20 pulse, output 5, DC 50%). 10 ml (500 mg) of the S-bead-DxAl-lysine particles are mixed with 34.5 ml of borate buffer. The following are then added to the mixture: 0.5 ml of a 10% Tween 20 solution and 1 ml of a succinic anhydride solution (10 mg in 100 ml of DMSO). The mixture is stirred at room temperature for 2 hours. A further 1 ml of a succinic anhydride solution (10 mg in 100 ml of DMSO) is added and the mixture is incubated at room temperature for 16 hours while being stirred. 10 ml of MES buffer (50 mM MES, pH 5.0) are then added and the mixture is centrifuged (30 minutes, 16,000 rpm, 10° C.). The supernatant is discarded and the pellet is resuspended in 40 ml. The washing procedure is repeated two to three times. In conclusion, the pellet is resuspended in approx. 8 ml of MES buffer (50 mM, 0.1% Tween 20, pH 5.0)

and homogenized with the Sonifier 250 (30 pulse, output 5, DC 50%). The rubella antigen is then coupled onto the particles.

EXAMPLE 10

Preparing Biotinylated Rubella Antigen

In order to prepare biotinylated rubella antigen, 6.5 ml of the rubella antigen solution (0.6 mg of rubella antigen/ml in 0.1 M $NaCO_3$/0.25% Tween) are mixed, while stirring, with 650 µl of biotin-X-NHS supplied by Pierce (1.2 mg/ml in DMSO). After 22 hours, the mixture is desalted on a Pierce desalting column (Pres toTM) using 0.05 M phosphate, 0.15 M NaCl, 0.25% Tween 20, pH 7.6.

EXAMPLE 11

Carrying Out an Immunoassay According to the Invention ("High-Dose Hook Assay")

10 µl of sample are mixed with 50 µl of a particle suspension (C-bead-ADx-DexAl coated with anti-human IgG antibodies, 50 µg/ml, Example 6), 50 µl of a rubella antigen-coated particle suspension (S-bead-DxAl coated with rubella antigen, 0.2 mg/ml; Example 9) and 50 µl of a biotinylated rubella antigen solution (5 µg/ml), and the mixture is incubated at 37° C. for 196 seconds (or 359 seconds). After these 196 seconds (359 seconds), the first signal (time T1) is recorded by luminescence. After a further 81 seconds (or immediately after T1, respectively), 50 µl of the S-bead-DxAl-SAv suspension (0.2 mg/ml) and 75 µl of assay buffer (0.1 M tris buffer, 0.3 M NaCl, 25 mM EDTA, 1 mg of BSA/ml, pH 8.2) are added to the mixture and the whole is incubated at 37° C. for 264 seconds. After that, the second signal (time T2) is recorded by luminescence.

EXAMPLE 12

Carrying Out a Standard Assay

10 µl of sample are mixed with 50 µl of particle suspension (C-bead-ADx-DxAl coated with anti-human IgG antibodies, 50 µg/ml, Example 6) and 50 µl of biotinylated rubella antigen solution (5 µg/ml), and the mixture is incubated at 37° C. for 277 seconds. After that, 100 µl of the S-bead-DxAl-SAv suspension (0.1 mg/ml) and 25 µl of assay buffer are added to the mixture and the whole is incubated at 37° C. for 264 seconds. After that, the signal (time T2) is recorded by luminescence.

The results of the different immunoassay formats are compared in Table 1:

The high-dose hook sample can now be determined with the aid of the signal magnitude at time T1 or with the aid of the signal magnitude at time T2 related to the T2 to T1 signal ratio. FIG. 2 clarifies this interrelationship. In the case of samples having relatively high titers, the signal at time T1 will also increase until the high-dose hook region is reached in this case as well. Consequently, the value for T2 to T1 will keep on decreasing, as will the value for the signal magnitude at time T2. Short incubation times (T1) may be more advantageous for being able to identify the high-dose hook sample more effectively (see FIG. 2 as well).

The invention claimed is:

1. A method for detecting an analyte A in a sample, comprising:
   (i) incubating an incubation mixture comprising a sample with an analyte A-specific binding partner R1, which is associated with a solid phase, an analyte A-specific binding partner R2, which is associated with a label L1, and an analyte A-specific binding partner R3, which is associated with a label L2, wherein binding partners R2 and R3 are selected such that saturation of analyte A-binding sites of the binding partner R2 requires a) a higher analyte A concentration, b) a longer incubation, or c) a higher analyte A concentration and a longer incubation, than does saturation of analyte A-binding sites of the binding partner R3; and
   (ii) determining an L1-dependent measurement signal at time T1 and an L2-dependent measurement signal or an L1 plus L2-dependent measurement signal at time T2, wherein time T1 is earlier than time T2, time T2 is after addition of label L2, and time T1 occurs before 30% of time from addition of label L2 to time T2 has elapsed; or determining an L1-dependent measurement signal using a first measurement method and an L2-dependent measurement signal or an L1 plus L2-dependent measurement signal using a second measurement method, wherein the first and second measurement methods are different.

2. The method of claim 1 for detecting an analyte A in a sample, wherein the method comprises a quantitative measurement.

3. The method of claim 1 for detecting an analyte A in a sample, wherein the method comprises a qualitative measurement.

4. The method of claim 1 for detecting an analyte A in a sample, wherein the method comprises at least one of detecting, avoiding, and decreasing a hook effect.

5. A method for detecting an analyte A in a sample, comprising:
   (i) incubating an incubation mixture comprising a sample with an analyte A-specific binding partner R1, which is

| Diluton of the high-dose hook sample | "High-dose hook assay" (short T1) T1 signal [counts] | "High-dose hook assay" (long T1) T1 signal [counts] | "High-dose hook assay" T2 signal [counts] | Standard assay T2 signal [counts] |
|---|---|---|---|---|
| Undiluted | 21495 | 96651 | 1260815 | 1477950 |
| 1:2.5 | 10202 | 52762 | 1986820 | 2314755 |
| 1:5 | 6785 | 34393 | 759392 | 1283560 |
| 1:10 | 4901 | 18097 | 498505 | 718458 |
| 1:20 | 3964 | 11551 | 323291 | 456184 |
| 1:40 | 3273 | 7399 | 192937 | 251804 |
| 1:60 | 3114 | 6257 | 127737 | 164181 |
| 1:100 | 2894 | 5461 | 71684 | 97251 | associated with a solid phase, an analyte A-specific binding partner R2, which is associated with a label L1, and an analyte A-specific binding partner R3, which is associated with a first member of a specific binding pair, wherein binding partners R2 and R3 are selected such that saturation of analyte A-binding sites of the binding partner R2 requires a) a higher analyte A concentration, b) a longer incubation, or c) a higher analyte A concentration and a longer incubation, than does saturation of analyte A-binding sites of the binding partner R3;

(ii) incubating the incubation mixture of (i) with a label L2, which is associated with a second member of the specific binding pair; and (iii) determining an L1-dependent measurement signal at time T1 and an L2-dependent measurement signal or an L1 plus L2-dependent measurement signal at time T2, wherein time T1 is earlier than time T2, time T2 is after addition of label L2, and time T1 occurs before 30% of time from addition of label L2 to time T2 has elapsed; or determining an L1-dependent measurement signal using a first measurement method and an L2-dependent measurement signal or an L1 plus L2-dependent measurement signal using a second measurement method, wherein the first and second measurement methods are different.

6. The method of claim 1 for detecting an analyte A in a sample, wherein the method is a heterogeneous or a homogeneous sandwich test.

7. The method of claim 1 for detecting an analyte A in a sample, wherein R1 and R2; R1 and R3; R1, R2, and R3; or R2 and R3 are the same binding partner.

8. The method of claim 1 for detecting an analyte A in a sample, wherein L1 and L2 are the same label.

9. The method of claim 1 for detecting an analyte A in a sample, wherein the solid phase is a suspendable solid phase.

10. The method of claim 9, wherein the suspendable solid phase comprises microparticles.

11. The method of claim 10, wherein the microparticles function as a label.

12. The method of claim 1 for detecting an analyte A in a sample, wherein the binding partner R2 is associated with a suspendable solid phase.

13. The method of claim 12, wherein the suspendable solid phase comprises microparticles.

14. The method of claim 13, wherein the microparticles constitute the label L1.

15. The method of claim 1 for detecting an analyte A in a sample, wherein, as a consequence of formation of a sandwich, components of a signal-forming system, which include at least one of L1 and L2, are brought to a distance from each other which permits an interaction between these components, and the extent of the interaction is measured.

16. The method of claim 15, wherein the interaction comprises an energy transfer.

17. The method of claim 15, wherein the signal-forming system comprises photosensitizers which are associated with microparticles and chemiluminescent substances which are associated with microparticles.

18. A method for detecting an analyte A in a sample, comprising:
(i) incubating an incubation mixture comprising a sample with an analyte A-specific binding partner R1, which is associated with a solid phase, an analyte A-specific binding partner R2, which is associated with a label L1, and an analyte A-specific binding partner R3, which is associated with a first member of a specific binding pair, and a label L2, which is associated with a second member of the specific binding pair, wherein binding partners R2 and R3 are selected such that saturation of analyte A-binding sites of the binding partner R2 requires a) a higher analyte A concentration, b) a longer incubation, or c) a higher analyte A concentration and a longer incubation, than does saturation of analyte A-binding sites of the binding partner R3; and (ii) determining an L1-dependent measurement signal at time T1 and an L2-dependent measurement signal or an L1 plus L2-dependent measurement signal at time T2, wherein time T1 is earlier than time T2, time T2 is after addition of label L2, and time T1 occurs before 30% of time from addition of label L2 to time T2 has elapsed; or determining an L1-dependent measurement signal using a first measurement method and an L2-dependent measurement signal or an L1 plus L2-dependent measurement signal using a second measurement method, wherein the first and second measurement methods are different.

19. The method of claim 18 for detecting an analyte A in a sample, wherein the method comprises at least one of detecting, avoiding, and decreasing a hook effect.

20. The method of claim 18 for detecting an analyte A in a sample, wherein the method comprises a heterogeneous or homogeneous sandwich test.

21. The method of claim 18 for detecting an analyte A in a sample, wherein the method comprises quantitatively or qualitatively detecting the analyte A in the sample.

22. The method of claim 5 for detecting an analyte A in a sample, wherein the method comprises quantitatively or qualitatively detecting the analyte A in the sample.

23. The method of claim 5 for detecting an analyte A in a sample, wherein the method comprises at least one of detecting, avoiding, and decreasing a hook effect.

24. The method of claim 5 for detecting an analyte A in a sample, wherein the method is a heterogeneous or a homogeneous sandwich test.

25. The method of claim 5 for detecting an analyte A in a sample, wherein R1 and R2; R1 and R3; R1, R2, and R3; or R2 and R3 are the same binding partner.

26. The method of claim 5 for detecting an analyte A in a sample, wherein L1 and L2 are the same label.

27. The method of claim 5 for detecting an analyte A in a sample, wherein the solid phase is a suspendable solid phase.

28. The method of claim 27, wherein the suspendable solid phase comprises microparticles.

29. The method of claim 28, wherein the microparticles function as a label.

30. The method of claim 5 for detecting an analyte A in a sample, wherein the binding partner R2 is associated with a suspendable solid phase.

31. The method of claim 30, wherein the suspendable solid phase comprises microparticles.

32. The method of claim 31, wherein the microparticles constitute the label L1.

33. The method of claim 5 for detecting an analyte A in a sample, wherein, as a consequence of formation of a sandwich, components of a signal-forming system, which include at least one of L1 and L2, are brought to a distance from each other which permits an interaction between these components, and the extent of the interaction is measured.

34. The method of claim 33, wherein the interaction comprises an energy transfer.

35. The method of claim 34, wherein the signal-forming system comprises photosensitizers which are associated with microparticles and chemiluminescent substances which are associated with microparticles.

36. The method of claim 18 for detecting an analyte A in a sample, wherein R1 and R2; R1 and R3; R1, R2, and R3; or R2 and R3 are the same binding partner.

37. The method of claim 18 for detecting an analyte A in a sample, wherein L1 and L2 are the same label.

38. The method of claim 18 for detecting an analyte A in a sample, wherein the solid phase is a suspendable solid phase.

39. The method of claim 18, wherein the suspendable solid phase comprises microparticles.

40. The method of claim 39, wherein the microparticles function as a label.

41. The method of claim 18 for detecting an analyte A in a sample, wherein the binding partner R2 is associated with a suspendable solid phase.

42. The method of claim 41, wherein the suspendable solid phase comprises microparticles.

43. The method of claim 42, wherein the microparticles constitute the label L1.

44. The method of claim 18 for detecting an analyte A in a sample, wherein, as a consequence of formation of a sandwich, components of a signal-forming system, which include at least one of L1 and L2, are brought to a distance from each other which permits an interaction between these components, and the extent of the interaction is measured.

45. The method of claim 44, wherein the interaction comprises an energy transfer.

46. The method of claim 45, wherein the signal-forming system comprises photosensitizers which are associated with microparticles and chemiluminescent substances which are associated with microparticles.

* * * * *